United States Patent [19]

Lee

[11] Patent Number: 4,652,690

[45] Date of Patent: Mar. 24, 1987

[54] OXIDATIVE DEHYDROGENATION OF ALKYL AROMATICS WITH CARBON MOLECULAR SIEVES

[75] Inventor: Carol S. Lee, Princeton, N.J.

[73] Assignee: Mobil Oil Corp., New York, N.Y.

[21] Appl. No.: 812,083

[22] Filed: Dec. 23, 1985

[51] Int. Cl.$^4$ ............................................. C07C 4/02
[52] U.S. Cl. ..................................................... 585/443
[58] Field of Search ......................................... 585/443

[56] References Cited

U.S. PATENT DOCUMENTS 4,447,665 5/1984 Wennerbery ........................ 585/662
4,560,818 12/1985 Chu ...................................... 585/443

FOREIGN PATENT DOCUMENTS 1155527 6/1969 United Kingdom ................. 585/443
0353538 12/1977 U.S.S.R. ............................... 585/443

OTHER PUBLICATIONS

Emig and Hoffman, "Action of Zirconium Phosphate as a Catalyst for the Oxydehydrogenation of Ethylbenzene to Styrene", Journal of Catalysis 84, pp. 15–26, (1983).

Minachev et al., *Zeolites*, No. 4, Jul. 1984, pp. 270–275.

*Primary Examiner*—Curtis R. Davis
*Attorney, Agent, or Firm*—Alexander J. McKillop; Michael G. Gilman; Edward J. Trojnar

[57] ABSTRACT

Carbon molecular sieves are used in the oxidative dehydrogenation of alkyl aromatic compounds, for example, in the dehydrogenation of ethylbenzene to styrene.

12 Claims, No Drawings

OXIDATIVE DEHYDROGENATION OF ALKYL AROMATICS WITH CARBON MOLECULAR SIEVES

BACKGROUND OF THE INVENTION

A variety of catalysts have been investigated for the oxidative dehydrogenation of alkyl aromatic compounds, particularly the dehydrogenation of ethylbenzene to styrene. A literature survey in Emig and Hoffman, "Action of Zirconium Phosphate as a Catalyst for the Oxydehydrogenation of Ethylbenzene to Styrene", *Journal of Catalysis*, 84, pp. 15–26, (1983) lists a number of such catalysts which include metal oxides such as aluminum and antimony oxide, and active carbon. The use of zeolites in oxidative dehydrogenation of hydrocarbons was investigated by Minachev et al and reported in ZEOLITES, No. 4, July 1984, pp. 270–275.

In accordance with this invention molecular sieve carbon is used as a oxydehydrogenation catalyst.

SUMMARY OF THE INVENTION

Alkyl aromatic compounds are catalytically dehydrogenated in the presence of an oxidizing agent and a molecular sieve carbon as a catalyst.

DETAILED DESCRIPTION OF THE INVENTION

The alkyl aromatic compounds suitable for oxidative dehydrogenation in accordance with this invention are particularly ethyl substituted benzenes such as ethylbenzene, diethylbenzene and ethyltoluenes such a para-ethyltoluene.

Molecular sieve carbons which are used as a catalyst in this invention are commercially available materials. The preferred carbons have a pore size of 5 to 7 Angstroms. They are distinguished from the active carbon disclosed as a catalyst in the Emig and Hoffman article, referred to above, by their pore size which is smaller than the 1 nm (10 Angstroms) pore size of the active carbon referred to by Emig and Hoffman.

The oxidative dehydrogenation reaction is generally conducted as in the prior art, except that generally lower temperatures are considered preferable. For example, prior art processes are often conducted at temperatures of up to 700° C. The process of this invention is advantageously conducted at 300° C. to 400° C., although higher temperatures can be used.

The oxidizing agent can be oxygen used as pure oxygen or air, or mixtures of air or oxygen and another gas. Sulfur dioxide and hydrogen sulfide have been widely used with oxygen in dehydrogenation reactions and can be used in the process of this invention. Steam has also been used and can be used in this process.

The following non-limiting examples are illustrative of the invention.

EXAMPLES 1-2

Oxidative dehydrogenation of ethylbenzene with air was compared at 300° C. over two types of molecular sieve carbon and over non-sieve charcoal. The molecular sieve carbons have pores of 5–7 A. Each catalyst was calcined one hour in air at 500° C. before use. The molecular sieve carbons give improved conversion and selectivity to styrene.

| Example | 1 | 2 | Comparative |
|---|---|---|---|
| Catalyst: | Carbosieve G[a] | MSC-V Carbon[b] | Coconut Charcoal |
| WHSV Ethylbenzene | 0.43 | 0.43 | 0.87 |
| Air | 3.5 | 3.5 | 3.5 |
| Temp, °C. | 300° C. | 300° C. | 300° C. |
| Ethylbenzene conversion to hydrocarbons (mole %) | 31.8 | 30.8 | 3.5 |
| CO + $CO_2$ | 0 | 0 | 1.1 |
| Selectivity to Styrene in Hydrocarbons (Wt %) | 96.4 | 95.1 | 72.6 |

[a]Supelco molecular sieve carbon with 5–7A pores.
[b]Calgon molecular sieve carbon with 5.0–5.5A pores.

Although the present invention has been described with preferred embodiments, it is to be understood that modifications and variations can be resorted to without departing from the spirit and scope of this invention, as those skilled in the art will readily understand. Such variations and modifications are considered to be within the purview and scope of the appended claims.

I claim:

1. A process for the oxidative dehydrogenation of an alkyl aromatic compound selected from the group consisting of ethylbenzene and ethyltoluene comprising contacting the alkyl aromatic compound and oxygen in the presence of a molecular sieve carbon having a pore size of 5 to 7 Angstroms.

2. The process of claim 1 in which said alkyl aromatic compound is ethylbenzene.

3. The process of claim 1 in which said alkyl aromatic compound is para-ethyltoluene.

4. The process of claim 1 which is conducted in the presence of hydrogen sulfide.

5. The process of claim 2 which is conducted in the presence of hydrogen sulfide.

6. The process of claim 3 which is conducted in the presence of hydrogen sulfide.

7. The process of claim 1 which is conducted at a temperature of about 300° C. to 400° C.

8. The process of claim 2 which is conducted at a temperature of about 300° C. to 400° C.

9. The process of claim 3 which is conducted at a temperature of about 300° C. to 400° C.

10. The process of claim 4 which is conducted at a temperature of about 300° C. to 400° C.

11. The process of claim 5 which is conducted at a temperature of about 300° C. to 400° C.

12. The process of claim 6 which is conducted at a temperature of about 300° C. to 400° C.

* * * * *